(12) United States Patent
Zabrouskov

(10) Patent No.: US 8,153,961 B2
(45) Date of Patent: Apr. 10, 2012

(54) METHODS FOR ACQUISITION AND DEDUCTIVE ANALYSIS OF MIXED FRAGMENT PEPTIDE MASS SPECTRA

(75) Inventor: Vladimir Zabrouskov, Santa Clara, CA (US)

(73) Assignee: Thermo Finnigan LLC, San Jose, CA (US)

( * ) Notice: Subject to any disclaimer, the term of this patent is extended or adjusted under 35 U.S.C. 154(b) by 486 days.

(21) Appl. No.: 12/550,659

(22) Filed: Aug. 31, 2009

(65) Prior Publication Data

US 2011/0049351 A1    Mar. 3, 2011

(51) Int. Cl.
    H01J 49/26  (2006.01)
(52) U.S. Cl. ......... 250/282; 250/281; 250/287; 250/288
(58) Field of Classification Search ................ 250/281, 250/282, 287, 288
    See application file for complete search history.

(56) References Cited

U.S. PATENT DOCUMENTS

| | | | |
|---|---|---|---|
| 6,285,027 B1 | 9/2001 | Chernushevich et al. | |
| 7,095,013 B2 | 8/2006 | Bateman et al. | |
| 7,230,234 B2 | 6/2007 | Kobayashi | |
| 7,297,940 B2 * | 11/2007 | Bern | 250/282 |
| 2004/0180446 A1 | 9/2004 | Thompson et al. | |
| 2005/0196809 A1 | 9/2005 | Kelleher | |
| 2005/0199804 A1 | 9/2005 | Hunt et al. | |
| 2006/0172430 A1 | 8/2006 | Kelleher et al. | |
| 2006/0186331 A1 | 8/2006 | Hartmer et al. | |
| 2006/0289737 A1 | 12/2006 | Bassmann et al. | |
| 2007/0069122 A1 * | 3/2007 | Augustin et al. | 250/288 |
| 2007/0154900 A1 * | 7/2007 | Schneider et al. | 435/6 |
| 2007/0158544 A1 | 7/2007 | Hartmer | |
| 2008/0014199 A1 * | 1/2008 | Nowakowski et al. | 424/141.1 |
| 2008/0044915 A1 | 2/2008 | Hunt et al. | |
| 2008/0093547 A1 | 4/2008 | Hartmer et al. | |
| 2009/0134321 A1 * | 5/2009 | Hoyes | 250/282 |
| 2009/0173878 A1 * | 7/2009 | Coon et al. | 250/282 |
| 2010/0179766 A1 * | 7/2010 | Kim et al. | 702/19 |

OTHER PUBLICATIONS

Xia et al., "Implementation of Ion/Ion Reactions in a Quadrupole/Time-of-Flight Tandem Mass Spectrometer," Anal. Chem. 2006, 78 (12), pp. 4146-4154.

Kaplan et al., "Electron Transfer Dissociation in the Hexapole Collision Cell of a Hybrid Quadrupole-Hexapole Fourier Transform Ion Cyclotron Resonance Mass Spectrometer," Rapid Commun. Mass Spectrom. 2008, 22, pp. 271-278.

Hartmer et al., "Data-Dependent Electron Transfer Dissociation of Large Peptides and Medium Size Proteins in a QTOF Instrument on a Liquid Chromatography Timescale," Rapid Commun. Mass Spectrom. 2009, 23, pp. 2273-2282.

* cited by examiner

*Primary Examiner* — Michael Logie
(74) *Attorney, Agent, or Firm* — Thomas F. Cooney

(57) ABSTRACT

A method for acquiring and analyzing polypeptide mass spectra comprising: creating first and second sets of fragmented ions using first and second fragmentation techniques; obtaining mass spectra of the first and second sets of fragmented ions; searching a database of fragments of a first fragment pair type and of a second fragment pair type to respectively provide a set of M ranked and a set of N ranked best matching polypeptide sequences; subtracting synthetic spectra corresponding to each of the M and N ranked sequences from the mass spectra to provide first and second sets of modified mass spectra; searching the database of fragments of the second fragment pair type and of the first fragment pair type to provide third and fourth sets of polypeptide sequences providing best matches to the first and second sets of modified spectra, respectively; and creating a cumulative ranking of the third and fourth sets.

17 Claims, 13 Drawing Sheets

METHODS FOR ACQUISITION AND DEDUCTIVE ANALYSIS OF MIXED FRAGMENT PEPTIDE MASS SPECTRA

FIELD OF THE INVENTION

The present invention relates to proteomics and the identification of polypeptides using mass spectrometry.

BACKGROUND OF THE INVENTION

Mass spectrometry has become the method of choice for fast and efficient identification of proteins in biological samples. Tandem mass spectrometry of peptides in a complex protein mixture can be used to identify and quantify the proteins present in the original mixture. Tandem mass spectrometers achieve this by selecting single m/z values and subjecting the precursor ions to fragmentation, providing product ions that can be used to sequence and identify peptides. The information created by the product ions of a peptide can be used to search peptide and nucleotide sequence databases to identify the amino acid sequence represented by the spectrum and thus identify the protein from which the peptide was derived. Analytical methods that compare the fragment ion pattern to theoretical fragment ion patterns generated computationally from sequence databases can be used to identify the peptide sequence. Such methods can identify the best match peptides and statistically determine which peptide sequence is more likely to be correct. The algorithms typically utilize mass-to-charge ratio (m/z) information for identification purposes of the various product ions.

Fragmentation can be provided by various methodologies and mechanisms. Ion activation techniques that involve excitation of protonated or multiply protonated peptides, include collision-induced dissociation (OD), and infrared multiphoton dissociation (IRMPD) for example, and have been used to identify sequences. In these dissociation methods, translational energy is imparted to the peptide and is converted into vibrational energy that is then distributed throughout the bonds of the peptide. When the energy imparted to a particular bond exceeds that required to break the bond, fragmentation occurs and product ions are formed. The cleavage may not always however, occur along the backbone of the peptide if, for example, the side-chain of the peptide has elements that inhibit cleavage along the backbone, by providing a lower energy pathway and cleavage site on a side-chain. This preferential cleavage of the side-chain bonds rather than the polypeptide bonds often results in the provision of information primarily about the side-chain sequences and not the peptide sequence.

Other mechanisms of fragmentation include for example, those in which the capture of a thermal electron is exothermic and causes the peptide backbone to fragment by a non-ergodic process, those that do not involve intramolecular vibrational energy redistribution. Such methodologies include Electron Capture Dissociation (ECD) and Electron Transfer Dissociation (ETD). ECD and ETD occur on a time scale that is short compared with the internal energy distribution that occurs in the CID process, and consequently, most sequence specific fragment forming bond dissociations are typically randomly along the peptide backbone, and not of the side-chains. Ions from side chain cleavage are generally not observed and thus ECD and ETD are thought to provide more complete information on primary structure of peptides. However, in addition to the fragment ions, peaks are generally seen for ions which have been subjected to neutral loss, such as water (−18 Da) for example.

Unfortunately, ECD cannot be performed with trap-type mass analyzers since the electrons created by the reaction do not typically retain their thermal energy long enough to be trapped, thus ECD is typically performed on an FT-ICR mass spectrometer. These instruments are expensive. ETD fragmentation provides an alternative to ECD that can be performed on the more-readily-available ion trap instruments. In ETD, analyte ions are reacted under controlled conditions with reagent ions of opposite polarity. The transfer of electrons between reagent and analyte ions (from the reagent ion to the analyte ions for analyte cations) produces dissociation of the analyte ions.

FIG. 1 depicts a nomenclature typically adopted (and used herein) for the fragments of peptides and proteins (see Roepstorff and Fohlman [Roepstorff, 1984], and Johnson et. al. [Johnson, 1987], both of which are incorporated by reference herein). The three possible cleavage points of the peptide backbone are called a, b and c when the charge is retained at the N-terminal fragment of the peptide and x, y and z when the charge is retained by the C-terminal fragment. The numbering indicates, which peptide bond is cleaved counting from the N- and the C-terminus respectively, and thus also the number of amino acid residues in the fragment ion. The number of hydrogens transferred to or lost from the fragment is indicated with apostrophes to the right and the left of the letter respectively. Peaks corresponding to ions that have lost ammonia (−17 Da) and water (−18 Da) are denoted, respectively, by superscript asterisks and circles to the right of the letter.

It has been observed that low-energy CID predominantly yields, when fragmentation is along the peptide backbone, fragment ions (ion products) of type a, b, and y; a*, b*, and y* and a°, b°, and y°. By contrast, ETD produces mainly c and z* fragment ions and to a much smaller extent a*, y ions and z' and c* ions. Thus, the two techniques can yield complementary information when performed on the same precursor ions during the same scan event. However, such mixed-fragment mass spectra can be difficult to model and interpret, using conventional analysis techniques. This is mainly because the higher number of features present in the spectra would have a higher chance of matching with decoy spectra. This would cause an increase in the false discovery rate. Conventional analysis techniques are designed to deal with spectra containing only one type of fragments (c/z or b/y). Thus, such mixed-fragment mass spectra require a different search approach than is generally employed in analyses of conventional spectra, in which only one type of fragments is expected.

SUMMARY

In this document, a new approach to the acquisition and deductive analysis of mixed-fragment peptide mass spectra is presented in which, as a first step, two types of fragmentations (e.g., CID and ETD), are carried out on same polypeptide analyte during a same scan event. Thereafter, the resulting mass spectrum, comprising fragments of mixed types (for instance, b/y and c/z types) is searched against the database with respect to one of the types of fragments (e.g., b/y) to yield a list of the M best matching peptide or polypeptide candidates and, also, is separately searched with respect to the other type of fragments (e.g., c/z), to yield an independent list of N best matching peptide or polypeptide candidates. Each candidate spectrum from the first list and each candidate spectrum from the second list is subtracted from the original spectrum so as to yield a set of M modified spectra and another set of N modified spectra. Each resulting modified spectrum can be searched again with the other fragment type.

The resulting peptide lists from both searches can be compared and ranked according to their cumulative matching scores after all searches. The candidate present in both lists and having the highest number of fragments matched (i.e., the highest cumulative matching score) would be the most likely correct answer.

DETAILED DESCRIPTION

The present invention addresses some of the shortcomings of the known art. The following description is presented to enable any person skilled in the art to make and use the invention, and is provided in the context of a particular application and its requirements. Various modifications to the described embodiments will be readily apparent to those skilled in the art and the generic principles herein may be applied to other embodiments. Thus, the present invention is not intended to be limited to the embodiments and examples shown but is to be accorded the widest possible scope in accordance with the features and principles shown and described. The particular features and advantages of the invention will become more apparent with reference to the appended FIGS. 1-10, taken in conjunction with the following description.

Before describing the invention in detail, a few terms that are used throughout the description are explained. As used in this specification, a peptide or polypeptide is a polymeric molecule containing two or more amino acids joined by peptide (amide) bonds. As used in this specification, a peptide typically represents a subunit of a parent polypeptide, such as a fragment produced by cleavage or fragmentation of the parent polypeptide using known techniques. Peptides and polypeptides can be naturally occurring (e.g., proteins or fragments thereof) or of synthetic nature. Polypeptides can also consist of a combination of naturally occurring amino acids and artificial amino acids. Peptides and polypeptides can be derived from any source, such as animals (e.g., humans), plants, fungi, bacteria, and/or viruses, and can be obtained from cell samples, tissue samples, bodily fluids, or environmental samples, such as soil, water, and air samples. The term "ion optical assembly", as used herein, may include various ion optical devices, such as electrostatic lenses, radio-frequency (RF) multipole ion guides or ion transfer tubes, used either singly or in combination, so as to provide ion focusing, ion cooling, ion separation, ion transport along a defined path or to otherwise assist in the efficient transport of ions through a mass spectrometer.

Figure 2:
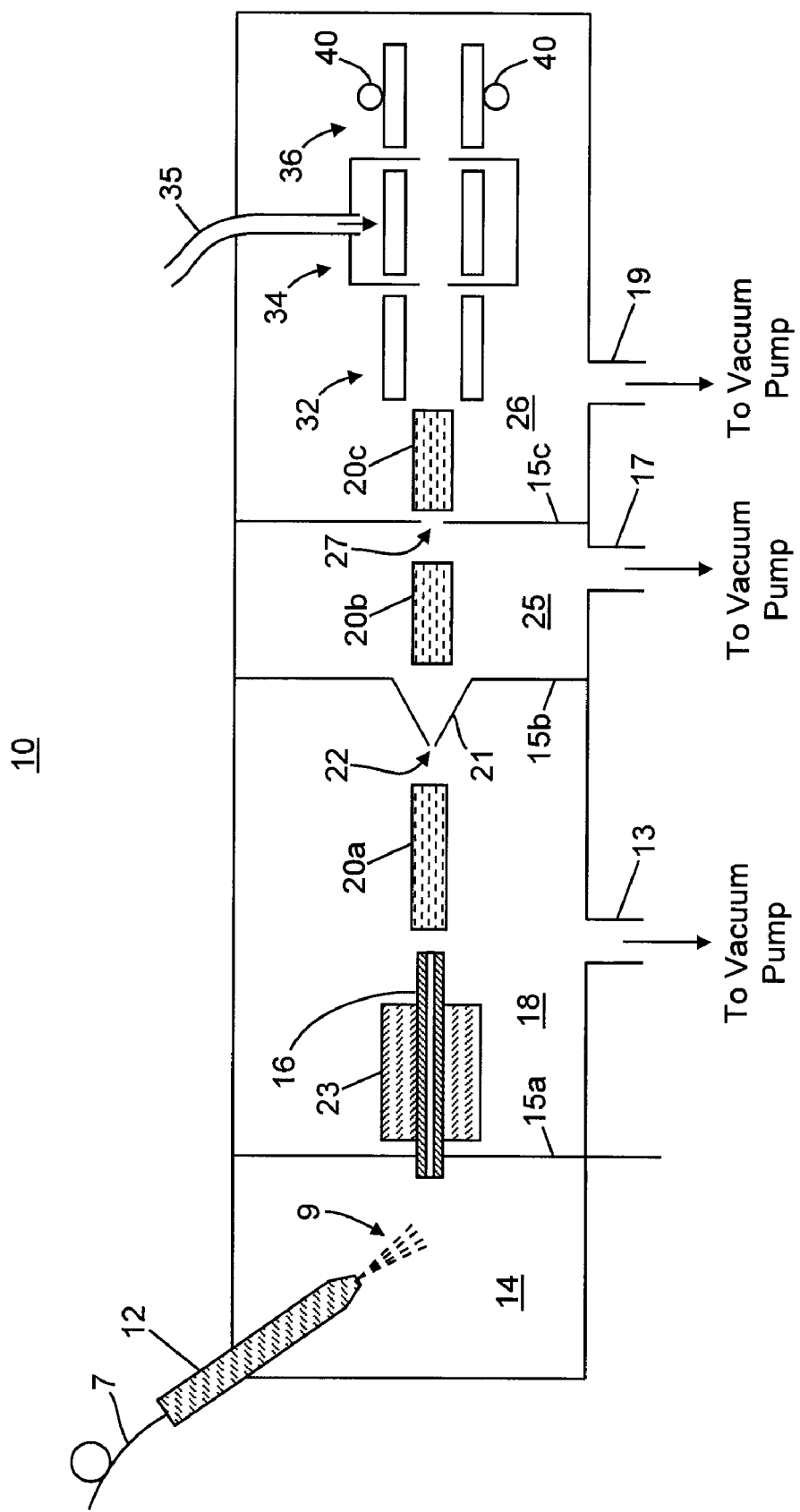
FIG. 2 is a schematic illustration of an example of a conventional ion trap mass spectrometer in which collisional ion dissociation may be performed.

FIG. 2 is a schematic illustration of an example of a conventional ion trap mass spectrometer system, shown generally at 10, capable of providing collisional ion dissociation. Referring to FIG. 2, an ion source 12 housed in an ionization chamber 14 is connected to receive a liquid or gaseous sample from an associated apparatus such as for instance a liquid chromatograph or syringe pump through a capillary 7. As but one example, an atmospheric pressure electrospray source is illustrated. However, any ion source may be employed, such as a heated electrospray ionization (H-ESI) source, an atmospheric pressure chemical ionization (APCI) source, an atmospheric pressure matrix assisted laser desorption (MALDI) source, a photoionization source, or a source employing any other ionization technique. The ion source 12 forms charged particles 9 (either ions or charged droplets that may be desolvated so as to release ions) representative of the sample, which charged particles are subsequently transported from the ion source 12 to the mass analyzer 36 in high-vacuum chamber 26 through intermediate-vacuum chambers 18 and 25 of successively lower pressure in the direction of ion travel. In particular, the droplets or ions are entrained in a background gas and transported from the ion source 12 through an ion transfer tube 16 that passes through a first partition element or wall 15a into an intermediate-vacuum chamber 18 which is maintained at a lower pressure than the pressure of the ionization chamber 14 but at a higher pressure than the pressure of the high-vacuum chamber 26. The ion transfer tube 16 may be physically coupled to a heating element or block 23 that provides heat to the gas and entrained particles in the ion transfer tube so as to aid in desolvation of charged droplets so as to thereby release free ions.

Due to the differences in pressure between the ionization chamber 14 and the intermediate-vacuum chamber 18 (FIG. 2), gases and entrained ions are caused to flow through ion transfer tube 16 into the intermediate-vacuum chamber 18. A second plate or partition element or wall 15b separates the intermediate-vacuum chamber 18 from a second intermediate-pressure region 25, likewise a third plate or partition element or wall 15c separates the second intermediate pressure region 25 from the high-vacuum chamber 26. A first ion optical assembly 20a provides an electric field that guides and focuses the ion stream leaving ion transfer tube 16 through an aperture 22 in the second partition element or wall 15b that may be an aperture of a skimmer 21. A second ion optical assembly 20b may be provided so as to transfer or guide ions to an aperture 27 in the third plate or partition element or wall 15c and, similarly, another ion optical assembly 20c may be provided in the high vacuum chamber 26 containing the mass analyzer 36. The ion optical assemblies or lenses 20a-20c may comprise transfer elements, such as, for instance a multipole ion guide, so as to direct the ions through aperture 22 and into the mass analyzer 36. The mass analyzer 36 comprises one or more detectors 40 whose output can be displayed as a mass spectrum. Vacuum ports 13, 17 and 19 may be used for evacuation of the various vacuum chambers.

It is to be understood that the mass spectrometer system 10 (as well as other such systems illustrated herein) is in electronic communication with a controller (not illustrated), which includes hardware and/or software logic for performing data analysis and control functions. Such controller may be implemented in any suitable form, such as one or a combination of specialized or general purpose processors, field-programmable gate arrays, and application-specific circuitry. In operation, the controller effects desired functions of the mass spectrometer system (e.g., analytical scans, isolation, and dissociation) by adjusting voltages (RF, DC and AC voltages provided by various not-illustrated power supplies) applied to the various electrodes of ion optical assemblies 20a-20c and quadrupoles or mass analyzers 32, 34 and 36, and also receives and processes signals from detectors 40. The controller may be additionally configured to store and run data-dependent methods in which output actions are selected and executed in real time based on the application of input criteria to the acquired mass spectral data. The data-dependent methods, as well as the other control and data analysis functions, will typically be encoded in software or firmware instructions executed by controller.

As illustrated in FIG. 2, the conventional ion trap mass spectrometer system 10 is a triple-quadrupole system comprising a first quadropole device 32, a second quadrupole device 34 and a third quadrupole device 36, the last of which is a mass analyzer comprising ion detectors 40. Various modes of operation are known. In many modes of operation, the first quadrupole device is operated as an ion trap which is capable of retaining and isolating selected precursor ions (that is, ions of a certain mass-to-charge ratio, m/z) which are then transported to the second quadrupole device 34. In many modes of operation, the second quadrupole device is employed as a fragmentation device which caused collision induced fragmentation of the selected precursor ions through interaction with molecules of an inert collision gas introduced through tube 35. The second quadrupole 34 may be operated as an RF-only device which functions as an ion filter; alternatively the second quadrupole may be operated as a second ion trap. The precursor or fragment ions are transmitted from the second quadrupole device 34 to the third quadrupole device 36 for mass analysis of the various ions.

Figure 1:
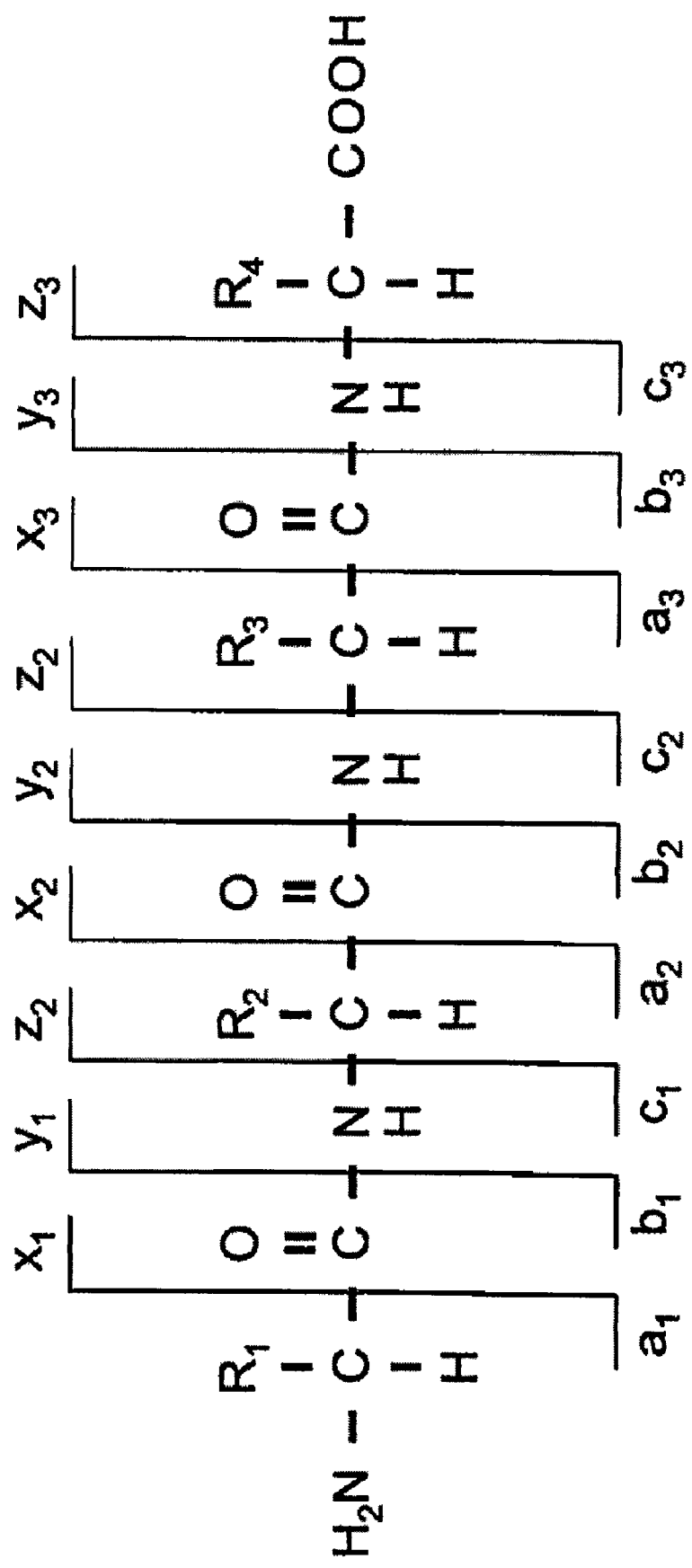
FIG. 1 is a depiction of nomenclature typically adopted for the fragment of peptides and proteins.
Figure 3:
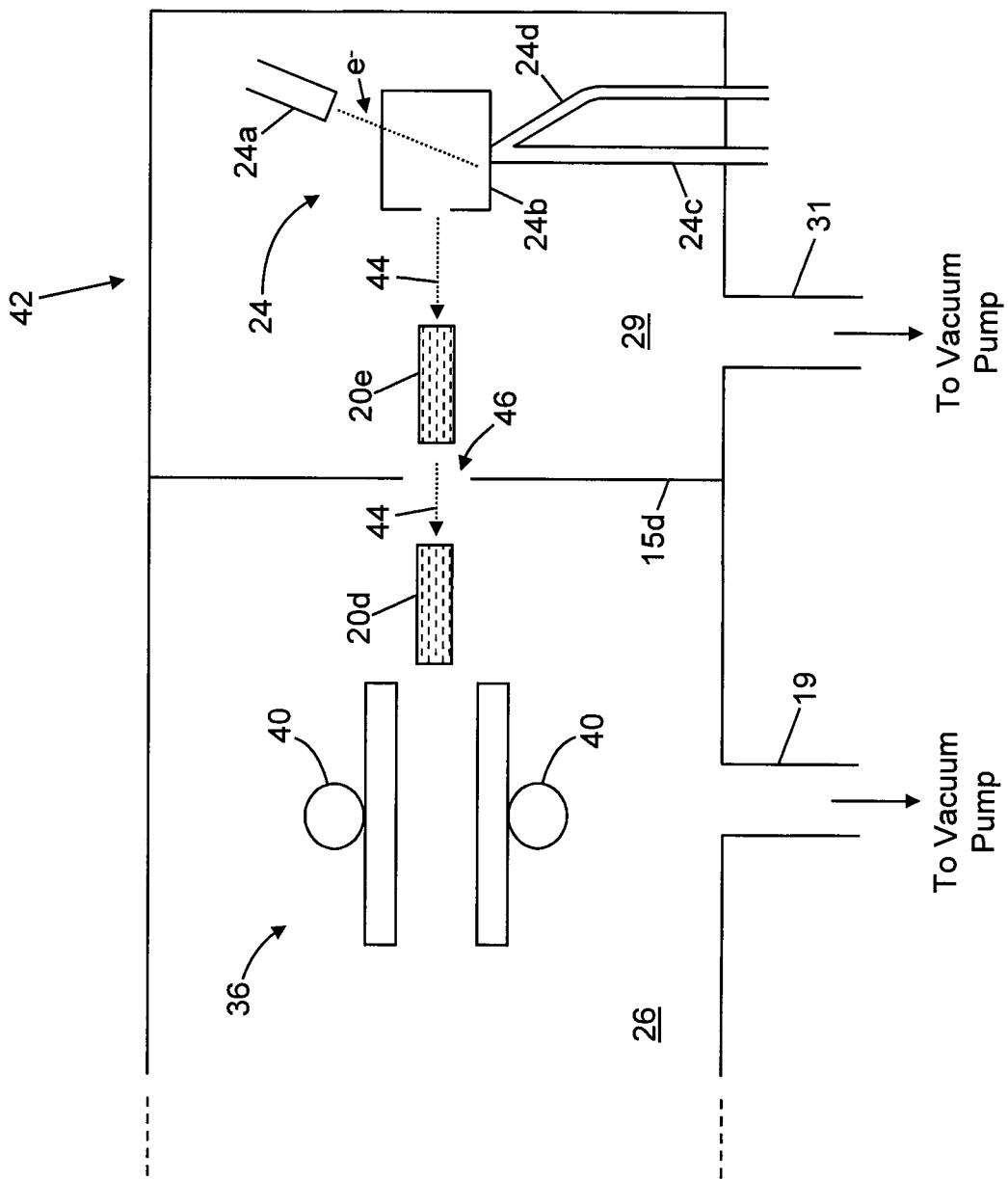
FIG. 3 is a schematic illustration of a portion of a multiple ion trap mass spectrometer in which both collisional ion dissociation electron transfer dissociation may be performed and on which the present teachings, in some of their aspects, may be practiced.

FIG. 3 is a highly schematic illustration of a portion of a second mass spectrometer system, the second mass spectrometer system adapted so as to provide the additional capability of performing electron transfer dissociation on selected precursor ions. Such a system has been described in detail in United States Patent Application Publication No. 2005/0199804 A1, which is incorporated by reference herein in its entirety. The mass spectrometer system shown in FIG. 2 comprises an additional chamber 42, which may be separately evacuated by means vacuum port 31, which is capable of providing reagent anions of section capable of providing reagent anions 44 into a high vacuum chamber 26 containing a mass analyzer 36 having detectors 40. The additional chamber 42 may be separated from the high vacuum chamber 26 by a partition element or wall 15d having an aperture 46 through which anions 44 pass into the high vacuum chamber for reaction with selected precursor cations. The anions may be guided and/or focused by means of ion optical assemblies or lenses 20d and 20e. The portions of the apparatus to the left of ion optical assembly 20d (not illustrated in FIG. 2) may comprise components of a conventional mass spectrometer as shown in FIG. 1 or various conventional modifications thereto. Fragment ions produced by CID may be introduced into the mass analyzer 36 as previously described with reference to FIG. 1.

The additional chamber 42 shown in FIG. 3 comprises a Negative Ion Chemical Ionization Source 24 comprising a filament 24a for providing a stream of electrons, various tubes, such as tubes 24c and 24d for introducing various reagent gases and a reaction chamber 24b in which anions are formed from the reagent gases by bombardment with electrons from the filament 24a. Operation of the apparatus shown in FIG. 3 to produce fragments by ETD may comprise the steps of introducing multiply charged cations into an ion trap device, such as the mass analyzer 36 or another quadrupole device configured and operated as an ion trap (for instance quadrupole device 34 of FIG. 2), introducing reagent anions 44 into the ion trap device, and then mixing the introduced reagent anions, or derivative reagent ions thereof, and the multiply charged cations, or derivative multiply charged cations thereof, so as to facilitate electron transfer from the reagent anions, or derivative reagent ions thereof, to the multiply charge cations, or derivative multiply charged cations thereof, to produce dissociation product cations. The mixing of the ions comprises superimposing the two ion clouds so that electron transfer takes place.

As described in United States Patent Application Publication No. 2005/0199804 A1, the ion trap device in which cations and anions are mixed may comprise a segmented multipole ion trap comprising a front set, center set and back set of electrode segments. The process of introducing anions and cations into the ion trap and allowing them to mix with one another may comprise the steps of injecting peptide cation precursor or fragment ions from one end of the segmented multipole ion trap and storing them in the front segment; injecting negative reagent ions into the same segmented multipole ion trap from the opposite end and storing them in the center segment; and then transferring the peptide cation precursor or fragment ions into the center segment and allowed to mix with the negative ions. After a defined reaction period, the anions are axially ejected, while the cation products are mass analyzed.

Various sequences of reaction or fragmentation steps are possible using the apparatus of FIG. 3. As a first example, CID-generated fragments may be analyzed in a first stage of analysis and ETD-generated fragments of the same precursor may be analyzed in a second stage of analysis. The first stage may be performed by isolating precursor ions in the first quadrupole 32, transferring a first portion of the isolated precursor ions to the second quadrupole 34; forming fragments ions by CID in the second quadrupole, transferring the CID-generated fragments to the mass analyzer (generally, a third quadrupole) 36 and analyzing the fragments using the mass analyzer 36. The second stage may be performed by transferring a second portion of the isolated precursor ions to the second quadrupole 34 (configured and operated as an ion trap) or through the second quadrupole to the mass analyzer 36, generating reagent anions in the Negative Ion Chemical Ionization source 24, transferring the reagent anions to the component containing the second portion of the precursor ions—either the mass analyzer 36 or through the mass analyzer to the second quadrupole, allowing the precursor cations and reagent anions to mix, ejecting ions other than the desired reaction products, transferring (if necessary) the reaction products to the mass analyzer 36 and analyzing the reaction products in the mass analyzer 36.

As a second example, CID may be performed so as to generate a first set of fragments from a precursor ion and then ETD may be performed so as to generate a second set of fragments from the first set of fragments or from a selected subset of the first set of fragments. The second set of fragments would then be analyzed in the mass analyzer 36. For example, this procedure may be accomplished by isolating precursor ions in the first quadrupole 32, transferring a first portion of the isolated precursor ions to the second quadrupole 34; forming fragments ions by CID in the second quadrupole 34, generating reagent anions in the Negative Ion Chemical Ionization source 24, transferring the reagent ions through the mass analyzer 36 to the second quadrupole 34, allowing the CID-generated cations and reagent anions to mix and react in the second quadrupole, ejecting ions other than the desired reaction products, transferring the reaction products to the mass analyzer 36 and analyzing the reaction products in the mass analyzer 36. Alternatively, the ETD and CID steps could be performed sequentially in the reverse order.

Although the ion trap mass spectrometer system 10 shown in FIG. 2 comprises multiple quadrupole ion traps, the functions performed by such multiple traps can be accomplished using a single ion trap. The alternative mass spectrometer system 10b illustrated in FIG. 4 comprises just one such "stand-alone" ion trap 36 and is shown including the additional chamber 42 having a Negative Ion Chemical Ionization Source 24. Reference numbers used in FIG. 4 refer to respective similar components already discussed in regards to prior figures. With an appropriate configuration and mode of operation, the single ion trap 36 may be utilized to perform the multiple steps of: (a) trapping a population of ions (assumed here to be cations) from a sample, (b) isolating a particular ion (that is, an ion of a particular m/z ratio) from the sample of ions by selectively ejecting ions comprising m/z ratios other than the desired ratio, (c) trapping a population of reagent anions, (d) causing the reagent anions to mix with and react with a portion of the isolated precursor ions so as to form, by the ETD process, a first population of fragment ions, (e) ejecting unreacted anions, and (f) causing the remaining precursor ions to fragment to form a second population of fragment ions mixed with the first population of fragment ions, the second population of fragments produced by the CID process, and (f) mass analyzing the mixed population of fragments.

Figure 4:
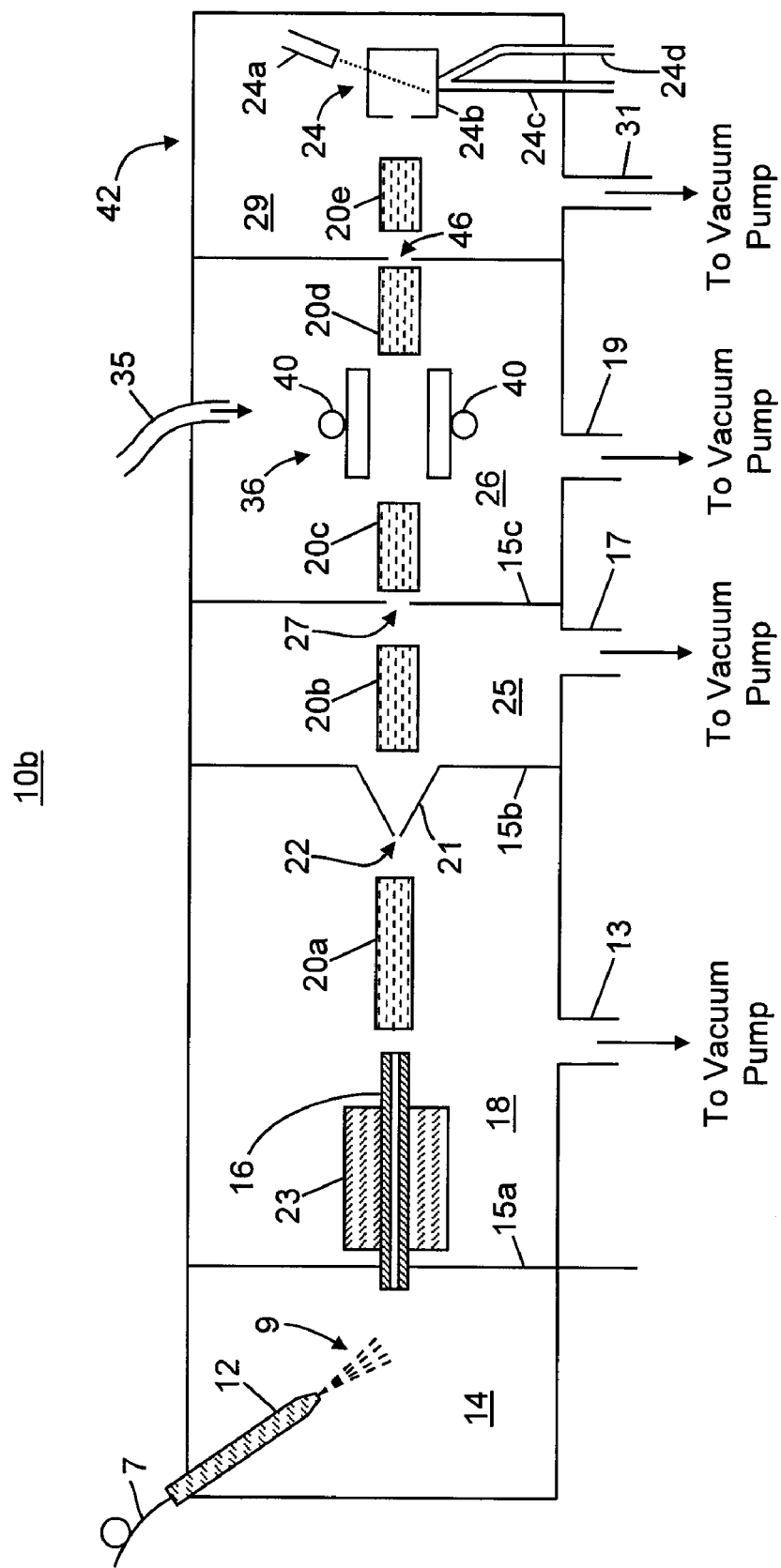
FIG. 4 is a schematic illustration of an ion trap mass spectrometer comprising a single ion trap in which both collisional ion dissociation electron transfer dissociation may be performed and on which the present teachings, in some of their aspects, may be practiced.
Figure 5A:
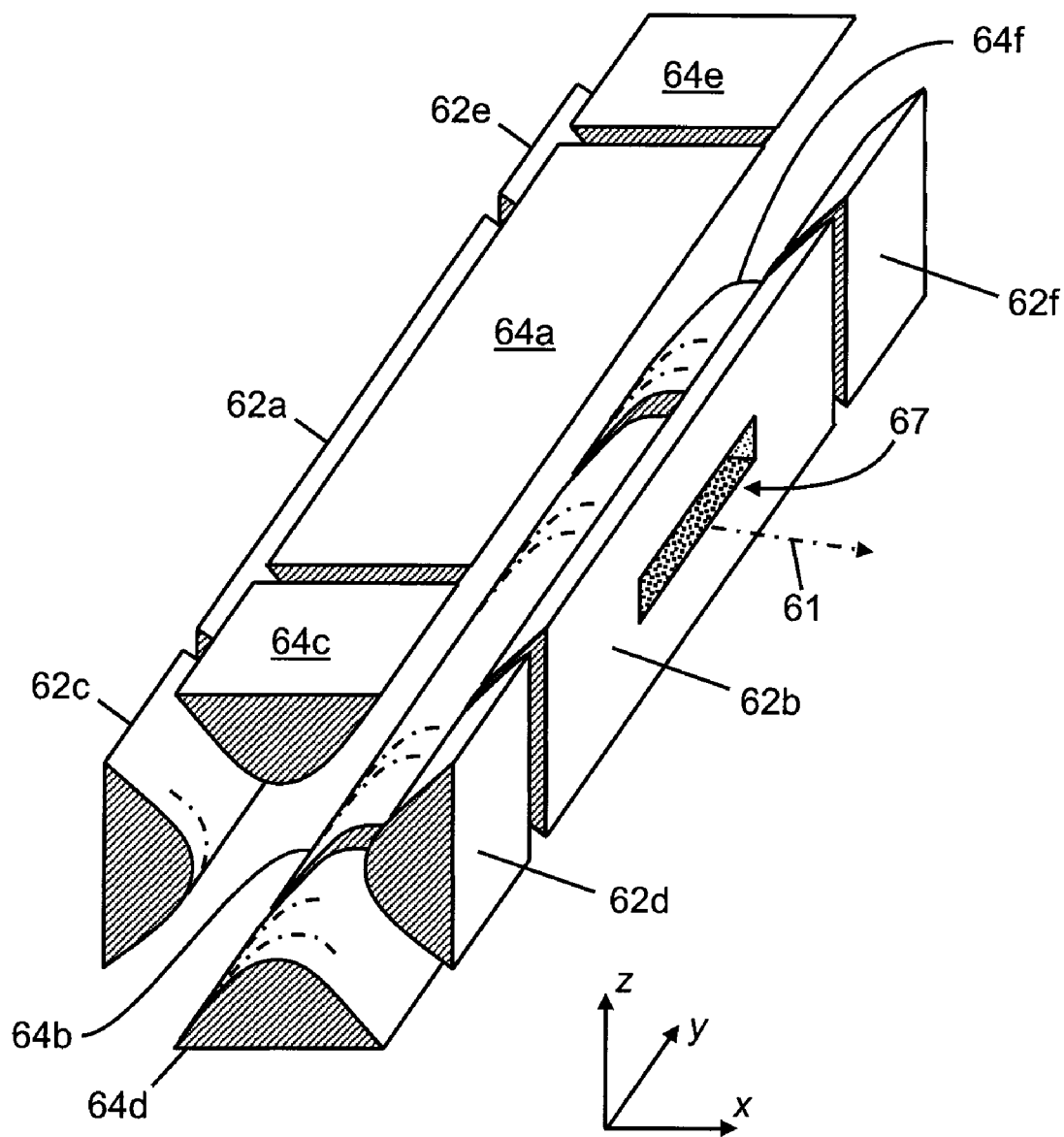
FIG. 5A is a perspective view of a first exemplary linear ion trap apparatus on which the present teachings, in some of their aspects, may be practiced.

FIG. 5A is a perspective view of a first exemplary quadrupole ion trap apparatus 36a which may be used as the stand alone ion trap 36 schematically shown in FIG. 4. The apparatus 36a comprises two central pairs of bar electrodes, comprising individual bar electrodes 62a, 62b, 64a and 64b. These electrodes are shown in FIG. 5A as extending parallel to the y-axis. Although these electrodes are shown as bars, either or both of the pairs of opposed electrodes (the pair consisting of electrodes 62a and 62b and/or the pair consisting of electrodes 64a and 64b) could be replaced by curved plate electrodes, possibly provided with apertures, such as aperture 61, for ejecting ions from the apparatus as, for instance, to a detector. These two pairs of electrodes comprise a center section of the ion trap 36a. Application, in known fashion, of DC voltages, RF voltages and, possibly, AC voltages to the center pairs of electrodes can permit trapping of ions in the xz-plane and ejection or scanning of ions by ejecting ions 61 through an aperture, such as aperture 67.

The four electrodes 62a, 62b, 64a and 64b are, by themselves, unable to trap ions in the y-dimension. Therefore additional pairs of opposed electrodes are provided at either end of the center section. A first pair of opposed electrodes—comprising individual electrodes 62c and 62d—and a second pair of opposed electrodes—comprising electrodes 64c and 64d—are provided at the front end of the apparatus. The electrodes 62c, 62d, 64c and 64d comprise a front section of the apparatus. At the opposite end are disposed a third pair of opposed electrodes—electrodes 62e and 62f—as well as a fourth pair of opposed electrodes—electrodes 64e and 64f. The electrodes 62e, 62f, 64e and 64f comprise a back section of the apparatus. During trapping, the four electrodes of the front section and the four electrodes of the back section may be held at DC voltage offsets relative to the center section electrodes so as to provide potential barriers at each end of the apparatus so as to confine ions within the ion trap. Also, as discussed in US Patent Application Publication 2005/0199804, the front and back sections may be used in conjunction with adjacent respective front and back ion lenses (not shown in FIG. 5A) to temporarily store cations and reagent anions, respectively, prior to mixing of these ions in the center section.

Figure 5B:
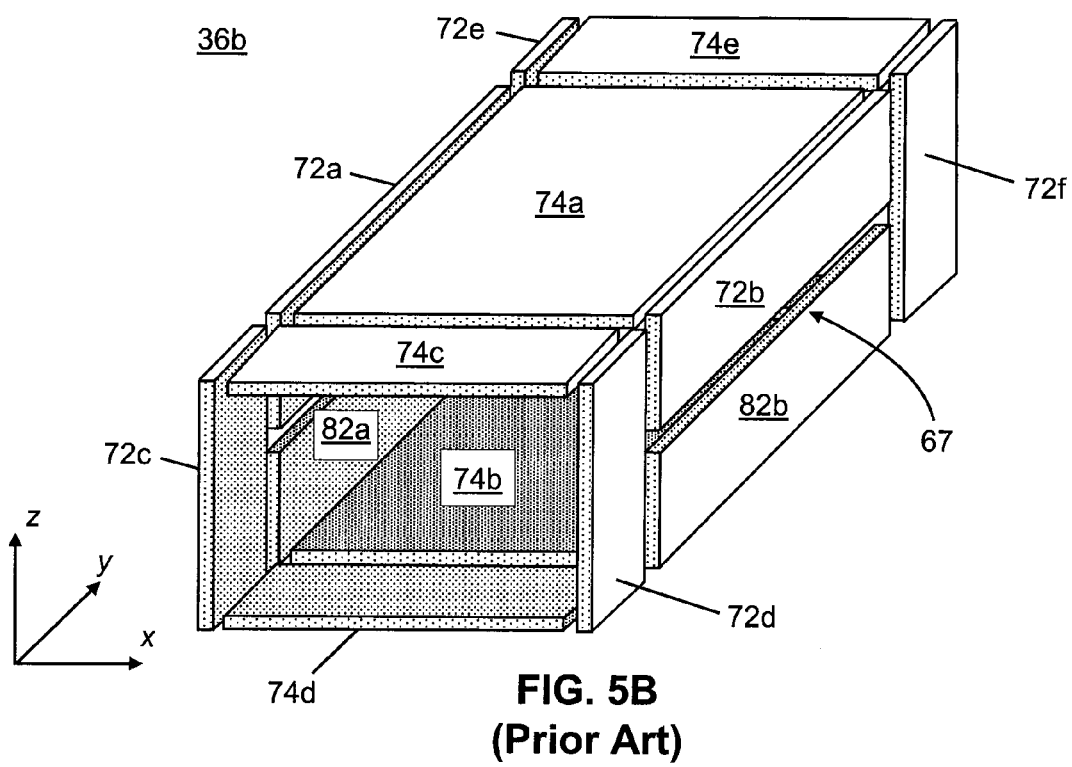
FIG. 5B is a perspective view of a Paul Trap quadrupole ion trap apparatus on which the present teachings, in some of their aspects, may be practiced.

FIG. 5B illustrates a rectilinear ion trap 36b as taught in U.S. Pat. No. 6,838,666, incorporated by reference herein in its entirety, and in a paper by Ouyang et al. (Ouyang, Z.; Wu, G;, Song, Y.; Li, H.; Plass, W. R.; "Rectilinear Ion Trap: Concepts, Calculations, and Analytical Performance of a New Mass Analyzer", Anal. Chem. 76, 2004, pp. 4595-4605), also incorporated herein by reference. The apparatus shown in FIG. 5B is an alternative ion trap apparatus which may be used as the stand alone ion trap 36 schematically shown in FIG. 4. The rectilinear ion trap (RIT) provides ease of manufacturing and miniaturization at the expense of some closeness of approximation to a pure quadrupolar field.

In the RIT 36b (FIG. 5B), plate electrodes 72a, 72b, 74a, 74b, 72c, 72d, 74c, 74d, 72e, 72f, 74e, 74f (note that the latter electrode is "hidden" from view and not shown in FIG. 5B) are utilized in place of the curved-surface bar electrodes of the linear quadrupole ion trap (FIG. 5A). Also, an additional set of plate electrodes, electrodes 82a and 82b, may be provided in the CIT such that apertures 67 are formed between the electrodes 72a and 82a and between the electrodes 72b and 82b. As with the linear ion trap (FIG. 5A), the MT (FIG. 5B) may be considered as comprising a front section (comprising electrodes 72c, 72d, 74c, 74d), a back section (comprising electrodes 72e, 72f, 74e, 740 and a center section (comprising the remaining electrodes) which may be utilized, for purposes of ETD, as described in US Patent Application Publication 2005/0199804.

Figure 6:
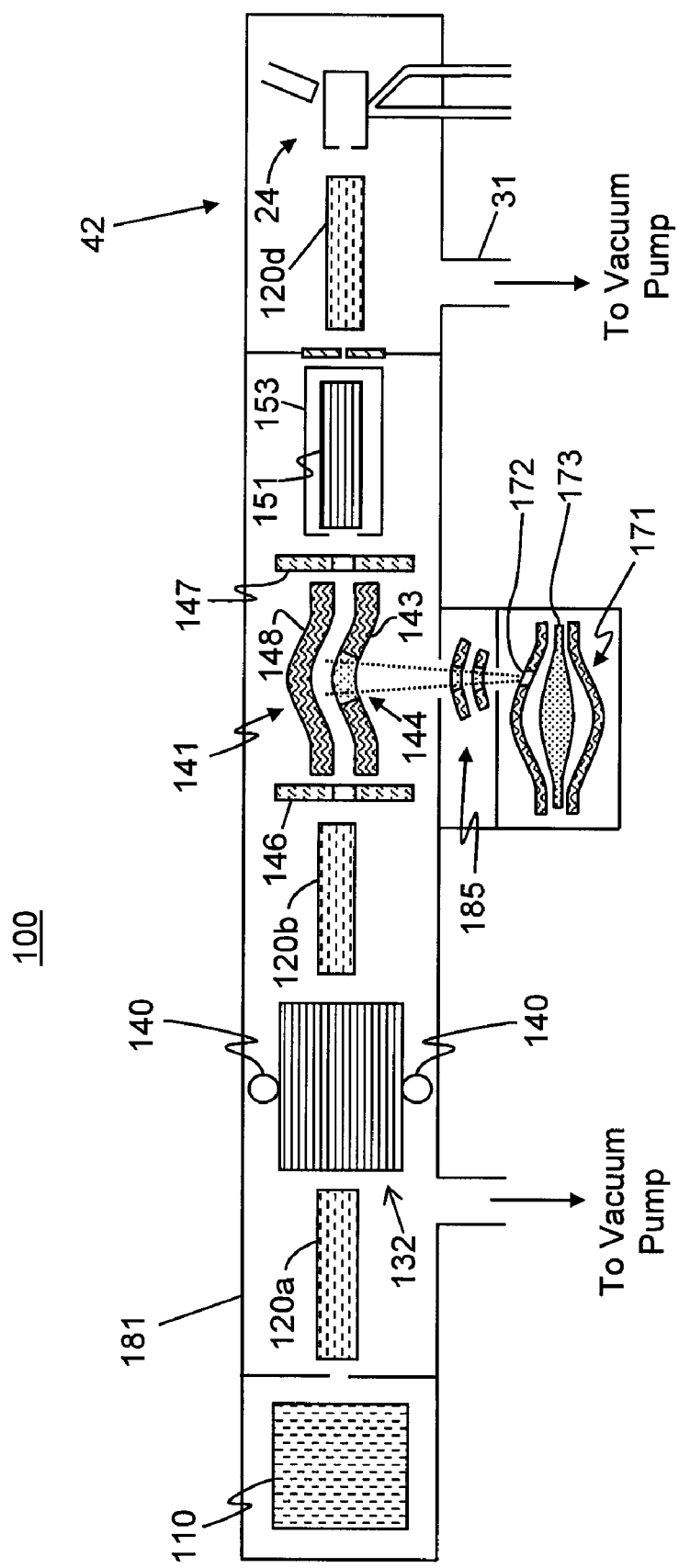
FIG. 6 is a schematic illustration of an electrostatic trap type (specifically, Orbitrap) mass spectrometer in which both collisional ion dissociation and electron transfer dissociation may be performed and on which the present teachings, in some of their aspects, may be practiced.

FIG. 6 illustrates another example of a mass spectrometer system 100 on which the invention according to some of its aspects may be practiced. The mass spectrometer system 100 shown in FIG. 6 comprises an electrostatic trap mass analyzer such as an Orbitrap mass analyzer 171. In the illustrated system, ions provided by ion source 110 are transferred to one or more evacuated chambers enclosed by housing 181. The ions are transferred or guided by a first ion optical assembly 120a and admitted to a first mass analyzer 132 (for instance, a multipole ion trap) having detectors 140 that has mass analysis and mass selection functionality and in which, optionally, collision induced fragmentation may be performed. Selected isolated ions or ion fragments are transferred, by means of second ion optical assembly 120b, from the first mass analyzer 132 to a curved quadrupole trap 141 (also known as a "C-trap") that has a slot 144 in an inner electrode 143. In operation the curved quadrupole trap 141 serves as an intermediate ion store which may acquire ions from either end and from which such acquired or accumulated ions may be injected into the electrostatic trap (e.g., Orbitrap) mass analyzer 171. Prior to ion injection, ions may be squeezed along the axis of the curved quadrupole trap 141 by raising voltages on end electrodes 146 and 147. For ion injection into the Orbitrap mass analyzer 171, the RF voltage on the curved quadrupole trap 141 is switched off, as is well known. Pulses are applied to electrodes 143 and 148 and to an electrode of curved ion optics 185 so that the transverse electric field accelerates ions into the curved ion optics 185. The converging ion beam that results enters the Orbitrap mass analyzer 171 through injection slot 172. The ion beam is squeezed towards the axis by an increasing voltage on a central electrode 173. Due to temporal and spatial focusing at the injection slot 172, ions start coherent axial oscillations. These oscillations produce image currents that are amplified and processed. Further details of the electrostatic trap apparatus 171 are described in International Application Publication WO 02/078046, U.S. Pat. Nos. 5,886,346, 6,872,938.

The system 100 shown in FIG. 6 optionally further comprises a reaction cell 151, which may comprise a collision cell (such as an octopole) that is enclosed in a gas tight shroud 153 and that is aligned to the curved quadrupole trap 141, as shown in FIG. 6. The reaction cell 153, when used as a collision cell, may be supplied with an RF voltage of which the DC offset can be varied. A collision gas line (not shown) may be attached and the cell is pressurized with nitrogen (or other) gas. Higher energy collisions (HCD) may take place in the system 100 as follows: Ions of a determined number, either mass selected or not, are transferred from the multipole ion trap 132 (MS 1) to the curved quadrupole trap 141. For HCD, ions are emitted from the curved quadrupole trap 141 to the octopole of the reaction cell 151 by setting a voltage on a trap lens. Ions collide with the gas in the reaction cell 151 at an experimentally variable energy which may be represented as a relative energy depending on the ion mass, charge, and also the nature of the collision gas (i.e., a normalized collision energy). Thereafter, the product ions are transferred from the reaction cell 151 back to the curved quadrupole trap 141 by raising the potential of the octopole. A short time delay (for instance 30 ms) is used to ensure that all of the ions are transferred. In the final step, ions are ejected from the curved quadrupole trap 141 into the Orbitrap analyzer 171 as described previously. HCD can be used to generate a series of ions which are typical of higher-energy fragmentation processes. The net outcome of such a procedure is the observation of some diagnostic ions which are not normally seen during conventional CID fragmentation, for instance, iminium ions which are characteristic of phosphotyrosine.

The system 100 further comprises an additional chamber 42 having a Negative Ion Chemical Ionization Source 24 and an additional ion optical assembly 120d as previously described with reference to FIG. 3. Reagent anions provided by the Negative Ion Chemical Ionization Source 24 may be transferred to either the reaction cell 151 or to the curved quadrupole ion trap 141 by setting voltages on electrodes of the ion optical assembly 120d, reaction cell 151 and curved ion trap appropriately. Either the reaction cell 151 or the curved quadrupole ion trap 141 may be utilized for mixing and reaction between the reagent anions and selected precursor ions are ion fragments as described previously.

In the system 100 shown in FIG. 6, collision induced fragmentation may be performed in either the multipole ion trap 132 or the curved quadrupole trap 141 or both. Higher energy collision fragmentation (HCD) may be performed in either the curved quadrupole trap 141 or the reaction cell 151. Likewise, reaction between analyte and reagent ions may be performed in either the curved quadrupole trap 141 or the reaction cell 151. Thus, the system 100 provides the flexibility to perform the three complementary and different fragmentation techniques of CID, HCD and ETD.

Multiple fill experiments may be performed in the system 100 as follows: Ions from the multipole ion trap 132 are injected multiple times into the curved quadrupole trap 141. Ions from the multipole ion trap 132 can be of the same type or they can be different, viz., mass isolated, collision activated, higher order collision activated, reacted with reagent anions delivered from the Negative Ion Chemical Ionization Source, etc. Multiple energy HCD experiments are performed by passing ions from the multipole ion trap 132, following each individual fill in the ion trap, into the reaction cell 151, here used as an ion store, at different collision energy offsets. The sum of fragment ions from all fills in the reaction cell are transferred to the curved quadrupole trap 141 where they are then ejected into the Orbitrap analyzer 171. Likewise, a population of ions can be built up in the curved quadrupole trap 141 through multiple fills from the multipole ion trap 132 and then sent to the reaction cell 151, or, alternatively, sent directly to the Orbitrap analyzer 171.

Figure 7:
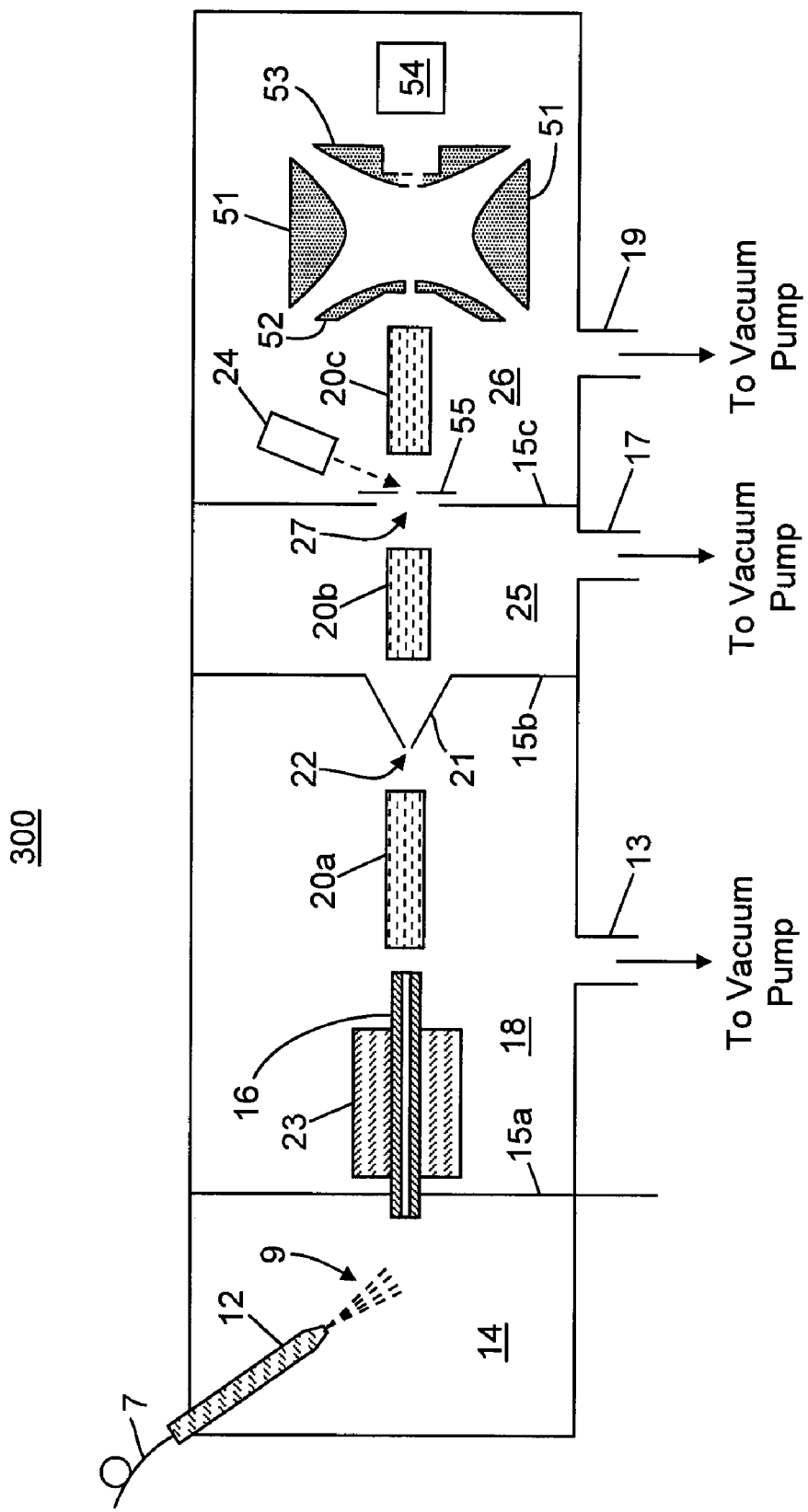
FIG. 7 is a schematic illustration of a quadrupole mass spectrometer in which both collisional ion dissociation electron transfer dissociation may be performed and on which the present teachings, in some of their aspects, may be practiced.

FIG. 7 is a schematic illustration of a quadrupole mass spectrometer system in which both collisional ion dissociation electron transfer dissociation may be performed. The system 300 shown in FIG. 7, which is modeled after the teachings of Hartmer et al. (US Patent Application Publication 2006/0186331), comprises a three-dimensional quadrupole ion trap (e.g., a Paul trap) comprising a ring electrode 51, a first end cap electrode 52, a second end cap electrode 53 and a detector 54. As taught by Hartmer et al., both positive analyte ions generated by ion source 12 as well as negative reagent ions generated by negative ion source 24 may be delivered to and mixed in the three-dimensional ion trap. As further taught by Hartmer et al., an ion switch 55 may be used to deflect negative ions onto a main ion path and through ion optical assembly 20c into an aperture of the first end cap 52. The ion switch 55 may comprise a split apertured diaphragm across whose two halves suitable DC potentials may be applied so as to either (a) allow ions from the ion source to pass through un-hindered from ion optical assembly 20b to ion optical assembly 20c or (b) to reflect reagent anions into and through ion optical assembly 20c. In this fashion, the positive and negative ions may be mixed and reacted in the three-dimensional quadrupole ion trap to effect electron transfer dissociation (ETD).

A collision or bath gas may also be introduced into the chamber 26 of system 300 (FIG. 7) so as to facilitate collision-induced dissociation by known methods. For instance, after ETD fragmentation, residual positively charged analyte ions may be further fragmented by CID fragmentation by introducing a suitable collision gas into the quadrupole ion trap and introducing a supplemental AC voltage of appropriate frequency to electrodes of the ion trap, in known fashion, so as to resonantly excite the energy level of only the precursor ions (but not of any of the prior-generated fragments). The excited energy state of the precursor ions will cause energetic collisions of the precursor ion with the collision gas so as to cause collision induced dissociation, thereby forming a second population of fragment ions mixed with the first population of fragment ions. This mixed population of fragment ions may be then be mass analyzed by scanning the trap in so as to sequentially eject ions according to m/z ratio, in known fashion. In this fashion, either ETD or CID or both may be performed on a same type of precursor ion in the same ion trap.

Figure 8A:
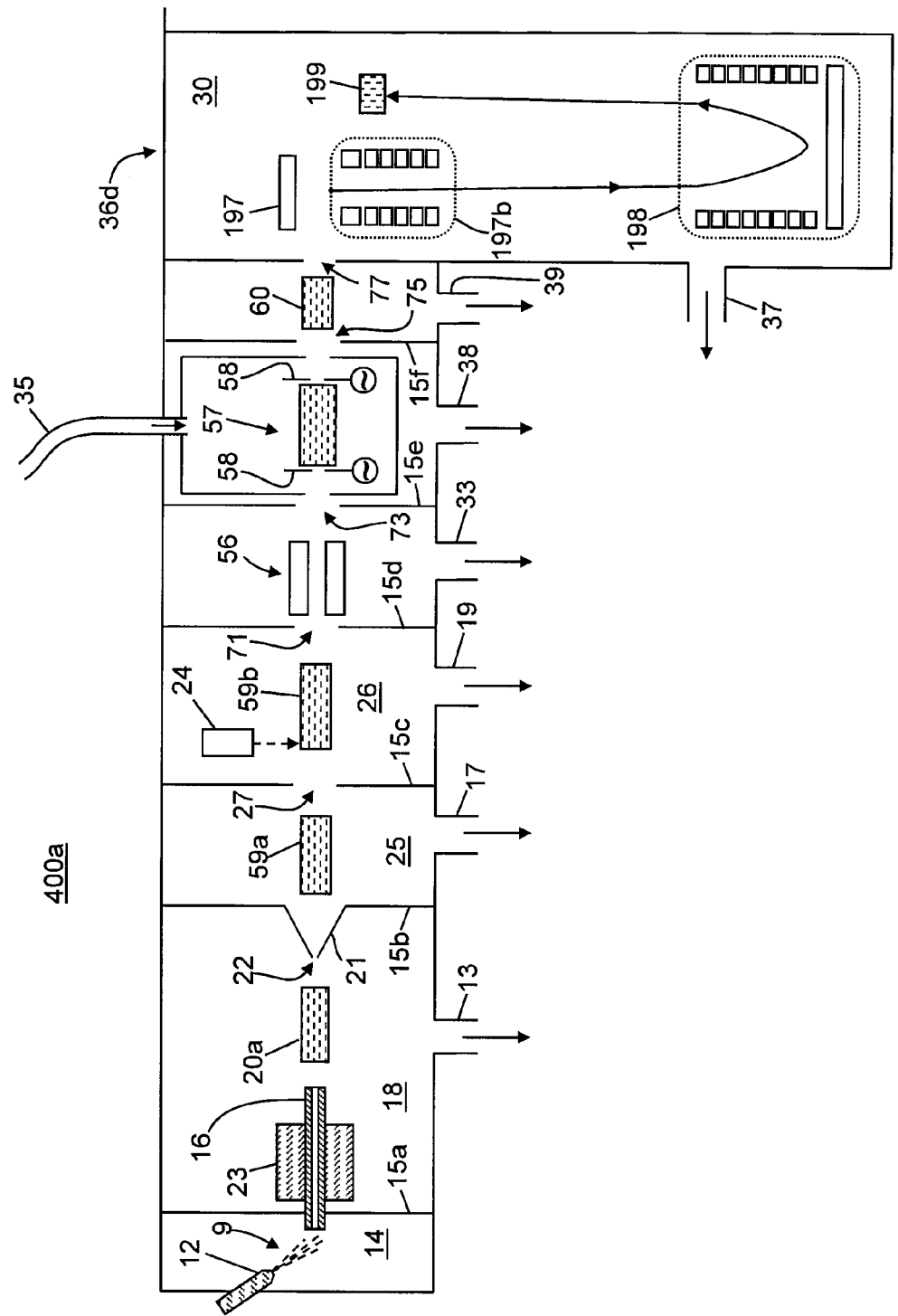
FIG. 8A is a schematic illustration of a first hybrid quadrupole/time-of-flight mass spectrometer in which both collisional ion dissociation electron transfer dissociation may be performed and on which the present teachings, in some of their aspects, may be practiced.
Figure 8B:
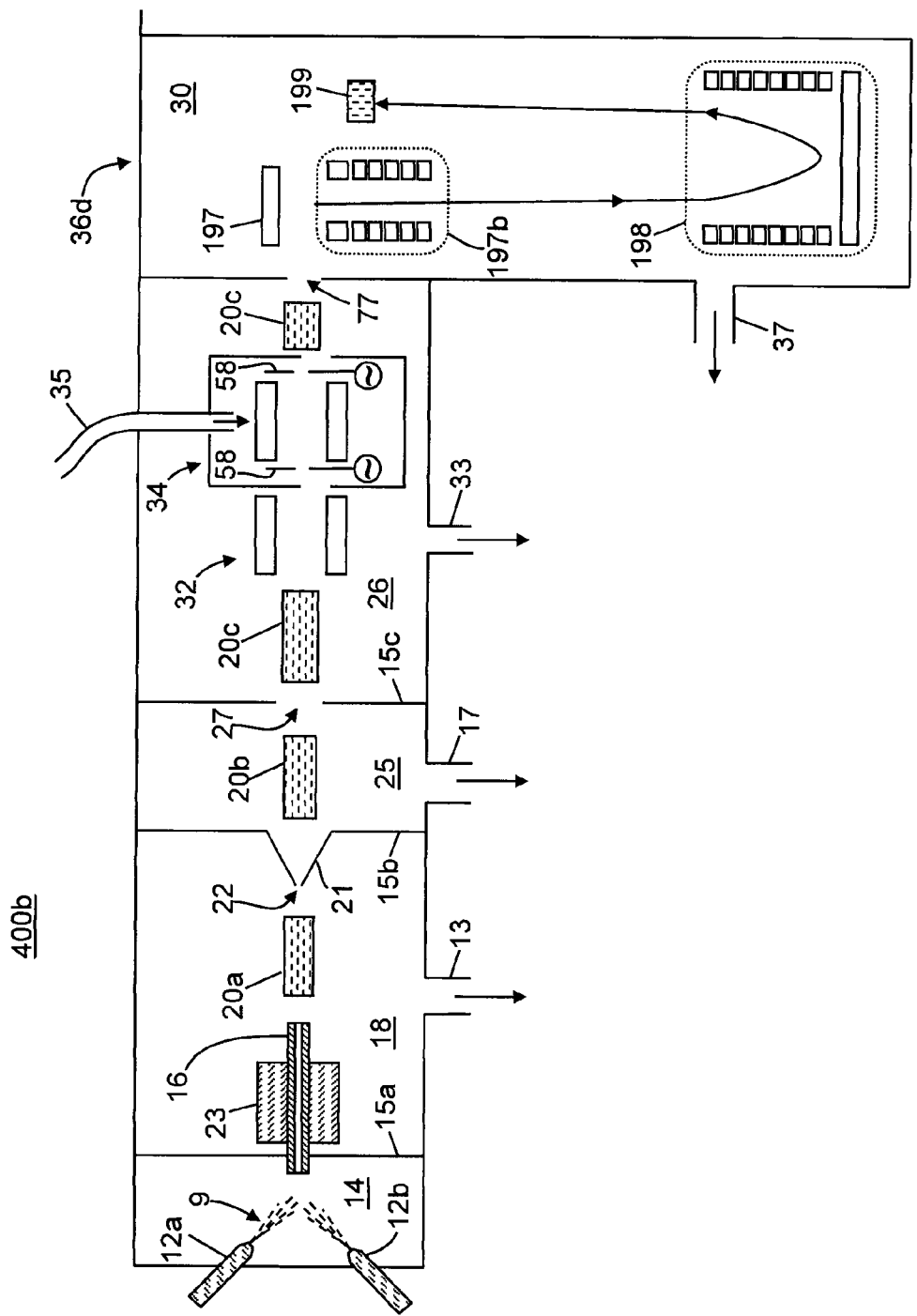
FIG. 8B is a schematic illustration of a second hybrid quadrupole/time-of-flight mass spectrometer in which both collisional ion dissociation electron transfer dissociation may be performed and on which the present teachings, in some of their aspects, may be practiced.

FIG. 8A-8B are schematic illustrations of two different hybrid quadrupole/time-of-flight mass spectrometer systems in which both collisional ion dissociation electron transfer dissociation may be performed. The system 400a shown in FIG. 8A and the system 400b shown in FIG. 8B each utilize an orthogonal acceleration time-of-flight (TOF) mass analyzer portion indicated as mass analyzer 36d in both figures. The time-of-flight mass analyzer 36d comprises a chamber 30 which may be evacuated by means of vacuum port 37.

The system 400a shown in FIG. 8A is modeled after the teachings of Kaplan et al. in a publication titled "Electron transfer dissociation in the hexapole collision cell of a hybrid quadrupole-hexapole Fourier transform ion cyclotron resonance mass spectrometer" (Rapid Commun. Mass Spectrom. 2008; 22: 271-278) as well as the teachings of Hartmer et al. in a publication titled "Data-dependent electron transfer dissociation of large peptides and medium size proteins in a QTOF instrument on a liquid chromatography timescale" (Rapid Commun. Mass Spectrom. 2009; 23: 2273-2282). Accordingly, the elements 59a and 59b are ion guides comprising respective octopole electrode rod sets, element 56 is an analytical quadrupole used, at least in part, for isolating a precursor cation of interest, element 57 is a hexapole reaction cell or collision cell and element 60 is an ion cooler formed as a hexapole electrode rod set. Optional partitions or walls 15a-15f separate various optional chambers having different operating pressures; apertures 22, 27, 71, 73, 75 and 77 permit ions to pass between such chambers. The respective chambers may be evacuated by means of vacuum ports 13, 17, 19, 33, 37, 38, and 39.

As previously described, sample cations are produced by ion source 12 of the system 400a. Additionally, a negative ion source 24 is disposed so as to radially inject reagent anions into the second octopole 59b through a region in which selected rods of the octopole 59b are slightly shortened relative to the other rods. Anions (from negative ion source 24) and cations (from ion source 12) may both be transferred to the hexapole reaction or collision cell 57 within which they may be allowed to mix and react. The reaction or collision cell 57 is bounded by entrance and exit lenses 58 to which alternating current (AC) may be applied so as to simultaneously axially trap both negative and positive ions within the cell. Further, a collision gas may be introduced into the reaction or collision cell 57 through tube 35 so as to provide a medium to enable CID of sample ions in the same cell. Analyte cations, which may be produced by reaction or collision in the cell 57, are transferred to the TOF 36b for analysis after cooling in ion cooler 60.

The alternative hybrid quadrupole/TOF system 400b shown in FIG. 8B is modeled after the teachings of Xia et al. in a publication titled "Implementation of ion/ion reactions in a quadrupole/time-of-flight tandem mass spectrometer" (Anal. Chem. 2006; 78: 4146-4154). In the system 400b, positive and negative ions are supplied to the same ion entrance by respective positive ion 12a and negative ion 12b sources. Multiple quadrupoles are employed within the instrument—as shown, quadrupole 32 is used as a mass filter or mass isolator and quadrupole 34 is used as a reaction or collision cell. Ion guide 20c may also comprise a quadrupole device. As discussed with reference to FIG. 8A, the quadrupole 34 is provided with entrance and exit lenses 58 to which AC voltage is applied so as to simultaneously trap positive and negative ions and within the quadrupole reaction/collision cell 34. Reaction between the positive and negative ions may then produce sample ion fragmentation by the ETD process. Collision gas for use in CID may be introduced into the quadrupole 34 through tube 35. Ions are transferred to the TOF mass analyzer 36d via ion optical assembly 20c, which may include an ion cooler.

In the orthogonal acceleration time-of-flight mass analyzer system 36d of the mass spectrometer systems 400a-400b (FIG. 8A), cations may be diverted from a flight path along a main axis (e.g., defined by a line between aperture 75 and aperture 77) by applying a voltage pulse to repeller plate 197 so as to divert a pulse of cations through accelerator lenses 197b. The accelerator lenses accelerate the cations, in a controlled fashion, so as to fly through a field-free region to reflectron 198. The cations are then reflected by reflectron 198 back through the field-free region of chamber 30 so as to intercept detector 199 for analysis in known fashion. The cations analyzed in this fashion may comprise any combination of precursor ions, fragments of precursor ions or other ion products that, prior to entering the mass analyzer, were either transmitted through, stored in or generated in an ion trap or reaction chamber. Either of the hybrid quadrupole/time-of-flight mass spectrometer systems, system 400a (FIG. 8A) or system 400b (FIG. 8B), may be used to perform both CID and ETD fragmentation on a same precursor ion population, so as to generate a mixed population of fragments derived from the two fragmentation procedures.

Figure 9:
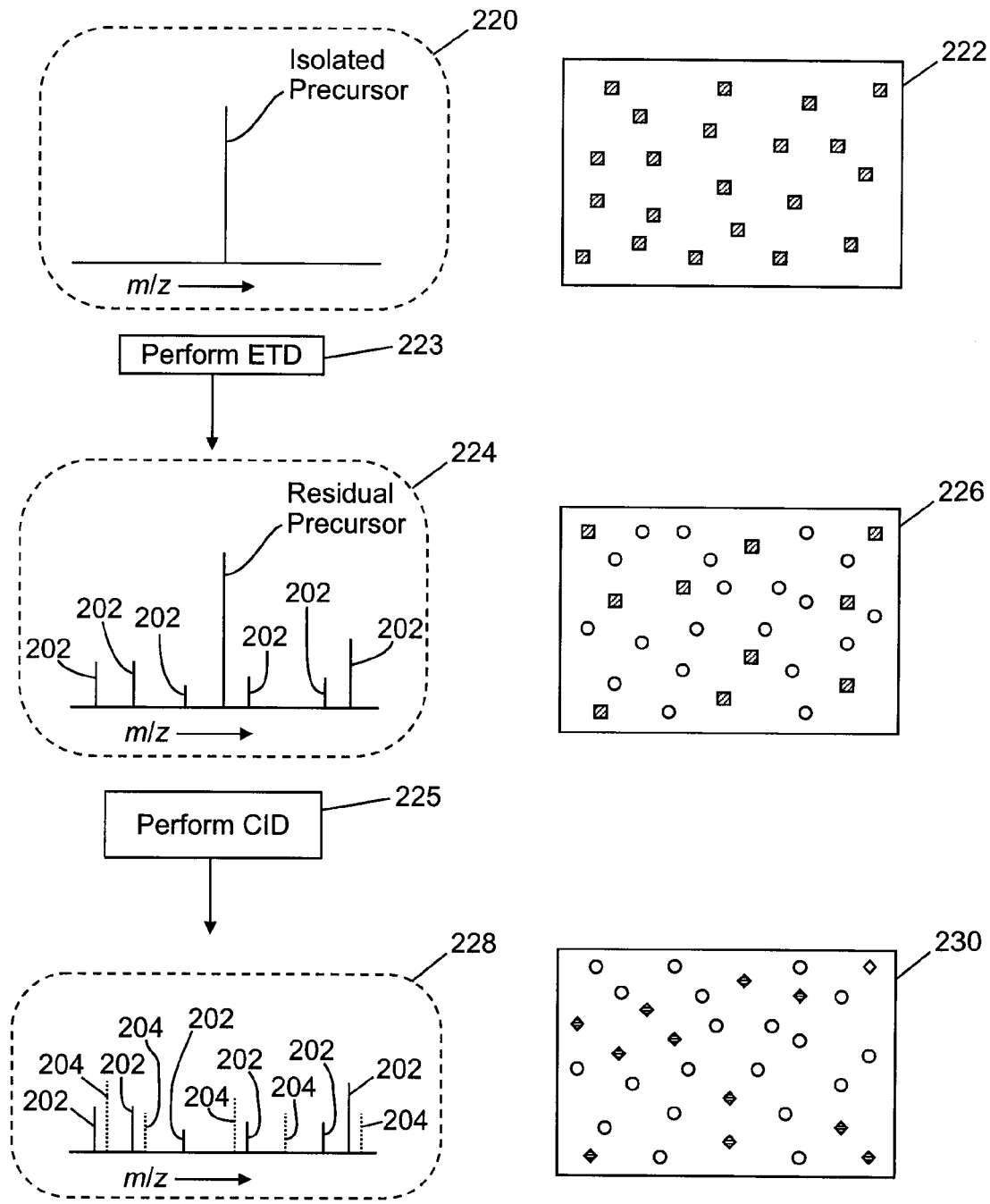
FIG. 9 is an illustration of a first method in accordance with the present teachings.

FIG. 9 illustrates, in greater detail, the ion populations produced in various of the above-described steps. Ideally, after generation of ions from a sample and elimination of all ions except for desired precursor ions, the ions remaining in an ion trap will comprise just the isolated population of precursor ions, represented as just a single line in a hypothetical m/z spectrum (box 220 of FIG. 9) and represented by shaded rectangles (without other symbols) in box 222 of FIG. 9. The isolated population of precursor ions may be generated by passing sample ions through an ion filter prior to transfer to the ion trap or may be produced by receiving various sample ions into the ion trap and ejecting unwanted ions from the ion trap. If the ion trap is configured as a reaction or fragmentation chamber, then subsequent reaction and fragmentation steps illustrated in FIG. 9 may be performed in the same ion trap, since resonant ejection may be used to eliminate unwanted reactions products while retaining desired reaction products. Alternatively, the isolated population of precursor ions and/or subsequent may be transferred to one or more other ion trap devices for temporary storage prior to mass analysis or to yet further reaction or fragmentation steps (so-called MS/MS/MS or even MS" operation). If, however, both the subsequent ETD step (step 223) and the CID step (step 225) are performed in a same ion trap, they should be performed in the order shown in FIG. 9.

In step 223 shown in FIG. 9, electron transfer dissociation (ETD) is performed according to methods discussed and referenced herein so as to cause a portion of the populated population of precursor ions to react to form fragments, while a population of residual precursor ions remains. A hypothetical m/z spectrum of ions at this stage is illustrated in box 224 of FIG. 9 in which the spectral line relating to the residual precursor ions co-exists with spectral lines 202 resulting from the presence of fragment ions. Box 226 of FIG. 9 schematically illustrates a "snapshot" of the ion population, with residual precursor ions represented by patterned rectangles and fragment ions represented by hollow circles (not distinguished according to m/z in box 226).

Subsequent fragmentation by collision induced dissociation (CID) in step 225 (FIG. 9) may exhaust the supply of precursor ions so as to yield the ion population schematically illustrated in box 230 in which the fragments generated by ETD (hollow circles) co-exist with fragments generated by CID (patterned diamonds). The different ion populations generally correspond to different fragment types (mostly b- and y-type ions produced by CID and c- and z-type ions produced by ETD). The ion population schematically represented in box 230 (which may comprise some residual precursor ions) is referred to, in this document, as a mixed population of fragment ions. The corresponding spectrum, shown in box 238, consisting of lines 202 corresponding to ETD-generated fragments and lines 204 corresponding to CID generated fragments (possibly with a line corresponding to a residual precursor ion), is referred to, in this document, as a mixed-fragment mass spectrum.

Figure 10:
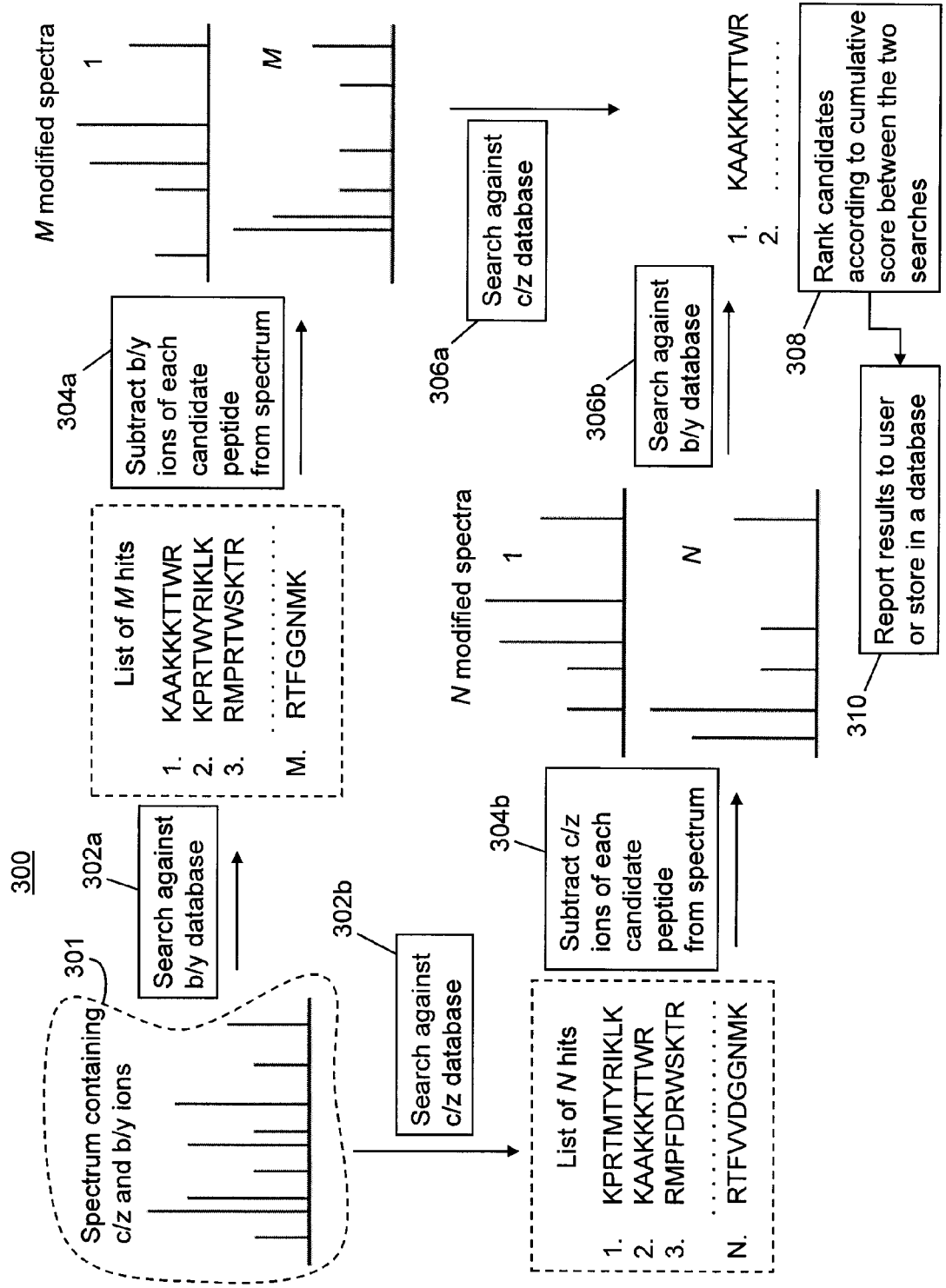
FIG. 10 is an illustration of a second method in accordance with the present teachings.

FIG. 10 is an illustration of a method 300 in accordance with the present teachings. In the first step, step 301, a mixed-fragment mass spectrum (a spectrum comprising information relating to more than one type of fragment pair) is experimentally obtained using instrumentation such as shown in FIG. 3 or FIG. 6 or modified versions thereof. The mixed-fragment mass spectrum is then searched (step 302a) against a polypeptide fragmentation database for one type of fragments (e.g., b/y) so at to yield a total of M best polypeptide sequence matches. Then (step 304a), synthetic spectra corresponding to each of the M best-matched sequences are subtracted from the original experimental spectrum so as to yield M modified spectra. The resulting M modified spectra can be searched again (step 306a) for another fragment type (e.g., c/z). The peptide lists from both searches can be compared and the same candidate peptide or polypeptide found in both databases and having the highest number of fragments matched would be given the highest score. The sequence of steps 302a through 306a is herein referred to as "Search 1".

Either simultaneously or sequentially with regard to the execution of Search 1, another search ("Search 2") is performed in the reverse order. In FIG. 10, steps 302b through 306b correspond to this reverse-order search. In Search 2, the original experimental spectrum is searched (step 302b) against the other type of fragment (e.g., c/z) to obtain a total of N best matches and spectra corresponding to each of the best matches are individually subtracted (step 304b) from the experimental spectrum so as to obtain a set of N modified spectra. These N modified spectra are then searched (step 306b) for the first fragment type (e.g., b/y). The candidate polypeptide sequence results from Search 1 and Search 2 are ranked according to their cumulative score calculated across the two searches in step 308. This approach should improve the confidence of the peptide identifications obtained from the spectra containing all four types of fragments (b/y and c/z). The search steps, steps 302a, 302b, 306a and 306b, may be performed using or with the assistance of a publicly or commercially available search program. One such example is described in a publication by Eng et al. (Eng. J. K.; McCormick, A. L., Yates III, J. R.; "An approach to correlate tandem mass spectral data of peptides with amino acid sequences in a protein database"; J. Am. Soc. Mass Spectrom. 1994, 5, pp. 976-989) incorporated herein by reference.

Figure 11:
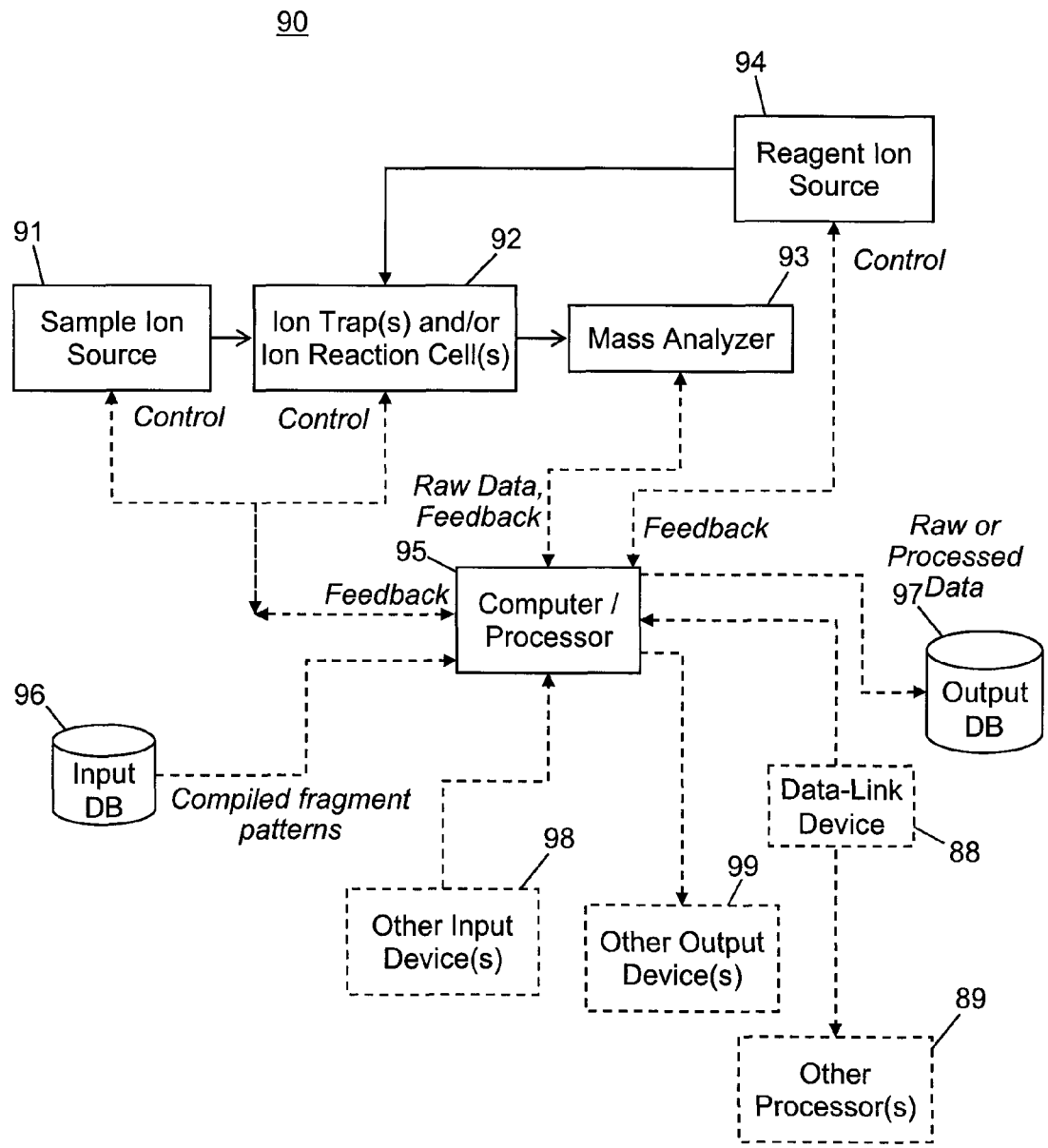
FIG. 11 is an illustration of a system in accordance with the present teachings.

Conveniently, various instrument control, monitoring, calculation and data retrieval and storage steps may be carried out automatically by a system including a computer or other electronic processor. Consequently, FIG. 11 is an illustration of a system in accordance with the present teachings that includes such a computer or other electronic processor. The system 90 illustrated in FIG. 11 comprises sample ion source (i.e., a source of sample ions, generally cations) 91; a reagent ion source (generally, a source of anions suitable for initiating ETD of selected sample ions or fragments or ion products thereof) 94; a module 92 comprising one or more ion traps or ion fragmentation or reaction cells, the module fluidically coupled to the sample ion source 91 and to the reagent ion source so as to receive sample ions and reagent ions, respectively; and a mass analyzer 94 fluidically coupled to the module 92 so as to receive sample ions, precursor ions, fragment ions or other product ions for analysis therein. The system 90 further comprises a computer or other electronic processor or controller 95 that is electronically coupled to the sample ion source 91, the module 92, the mass analyzer 93 and the reagent ion source 94 so as to provide programmatic control instruction to and receive operational data (feedback) from those devices. The system 90 further comprises a tangibly-embodied computer-readable medium comprising an input database 96 and a tangibly-embodied computer-writeable medium comprising an output database 96. These tangibly-embodied computer-readable and writeable media, which may, in fact, be the same tangibly-embodied medium may be embodied as or on a magnetic disk drive, a floppy disk, a magnetic tape, an optical disk such as a CD or DVD, a memory card, USB flash memory, etc. The tangibly-embodied computer-readable medium having the input database 96 (or another tangibly-embodied computer-readable medium) may also comprise computer or processor instructions for carrying out instrument control steps or other method steps in accordance with the present teachings. Optionally, the computer/processor 95 may further be electronically coupled to one or more other output devices 97, such as display screens, printers, etc. and/or one or more other input devices 98, such as keyboards, internet connections, etc.

Dashed connecting lines in FIG. 11 represent connection pathways that carry electronic signals and the flow of electronic signal information. Arrows on the various connecting lines represent possible direction of flow of information or, in the case of solid lines, ion propagation direction. The connecting lines between the mechanical components implicitly include any necessary ion transfer optics or ion optical assemblies, etc. The mechanical components, themselves, include any necessary power supplies, housings, vacuum lines, etc., even though such ancillary components may not be explicitly shown in the accompanying drawings, for reasons of clarity.

In the system 90 (FIG. 11), the electronic connections between the computer/processor 95 and the sample ion source 91, the reagent ion source 94, the mass analyzer 93, and the ion trap(s) or reaction cells 92 provide a pathway for operational commands to be sent from the computer/processor 95 to these other components. Such commands may include commands for starting and/or stopping one or more ion generation or transfer steps according to the methods taught herein and will generally include specific commands to apply (or stop applying) certain voltages to various electrodes or ion optics of the ion sources, ion traps, and ion reaction cells. These control lines may also transfer information from various sensors or detectors back to the computer/processor 95. Information sent from the mass analyzer 93 to the computer/processor 95 will include the raw experimental data, relating to m/z ratios of detected ions, for example, the spectrum illustrated with regard to step 301 of method 300 (FIG. 10). Other information sent to the computer/processor 95 from the mass analyzer 92, the sample ion source 91, the reagent ion source 94 and/or the ion trap(s) or reaction cell(s) 92 may include monitor or feedback signals from sensors of these components (for instance, temperature sensors, pressure sensors, ion filling level sensors, etc.) which relate to operational performance.

As illustrated in FIG. 11, the computer/processor 95 may be in electronic communication with a tangibly-embodied computer-readable medium having at least one input database 96 which contains, at least, information used to conduct the searches indicated in steps 302a, 302b, 306a and 306b of method 300 (FIG. 11). The same tangibly-embodied computer-readable medium may also comprise computer-readable instructions used to conduct various instrumental control and data processing steps in accordance with the present teachings, such as instructions to perform the steps outlined in the method 300. The computer/processor 95 may also be in electronic communication with a tangibly-embodied computer-readable medium having at least one output database 97 which contains, at least, results of data collecting and processing steps as taught herein, such as the results of identification and ranking of candidate peptides or polypeptides as shown, for instance, in steps 308 and 310 of method 300. Other input devices 98 and output devices 99 may be employed to receive information from or send information to a user, the internet, a local network, a printer, a data display device, etc.

Still with reference to FIG. 11, it is noted that the computer/processor 95 may optionally be electronically connected—either through the Internet or as part of an interconnected intranet other private network of computers, such as a local area network—using one or more data-link devices 88 to one more other processors 89 which may share some or all of the calculation load. It is known that the search steps, for instance steps 302a, 302b, 306a and 306b of method 300 shown in FIG. 10 can require significant calculation time. On the other hand, a user, such as an analytical chemist or instrumental technician, may have a need or desire to have access to and to be able to store results of data processing steps (e.g., final and/or intermediate results associated with the method 300) in "real-time"—that is, simultaneously with data acquisition. For simple compounds or with the use of a relatively fast computer or processor, such real time accessing, display or storage of calculation results may be possible utilizing just the computer/processor 95 shown in FIG. 11. However, whereas spectral acquisition time is on the order of only seconds or less, calculations may require up to several minutes of processor time if a sample comprises one or more complex polypeptides. Under such circumstances, a single processor may be insufficient to keep up with the calculation load. However, networked, parallel versions of search programs are known which are designed to run on a cluster of computers, for instance the program called SEQUEST-PVM (Sadygov, R. G.; Eng, J; Durr, E; Saraf, A.; McDonald, H.; MacCoss, M. J.; Yates, J. R.; "Code developments to improve the efficiency of automated MS/MS spectra interpretation"; Jour. Proteome Research, 2002, 1, pp. 211-215). In some instances, off-loading of some or the entire calculation burden to the one more other processors 89 may enable results to be obtained sufficiently quickly to enable real-time provision of calculation results. In such instances, raw or intermediate data may be sent to the one more other processors 89 at the same time that the computer/processor 95 continues to perform instrument control and monitoring and raw data acquisition functions. The results of the calculations performed by the one more other processors 89 are subsequently sent to the computer/processor 95 for display or output to a user or for storage in the output database 97.

The discussion included in this application is intended to serve as a basic description. Although the present invention has been described in accordance with the various embodiments shown and described, one of ordinary skill in the art will readily recognize that there could be variations to the embodiments and those variations would be within the spirit and scope of the present invention. The reader should be aware that the specific discussion may not explicitly describe all embodiments possible; many alternatives are implicit. Accordingly, many modifications may be made by one of ordinary skill in the art without departing from the spirit, scope and essence of the invention. Neither the description nor the terminology is intended to limit the scope of the invention. Any publications, patents or patent application publications mentioned in this specification are explicitly incorporated by reference in their respective entirety.

What is claimed is:

1. A method for acquiring and analyzing one or more mass spectra of a sample of a polypeptide or protein, the one or more mass spectra comprising information relating to more than one type of fragment pair, the method comprising:
    ionizing the sample so as to create ions of the sample;
    fragmenting selected ions of the sample using a first and a second fragmentation technique so as to create a first set and a second set of fragmented ions, respectively;
    mass analyzing a mixture of the first and second sets of fragmented ions using a mass analyzer so as to provide the one or more mass spectra;
    searching a database of polypeptide fragments of a first fragment pair type and a database of polypeptide fragments of a second fragment pair type so as to respectively provide a set of M ranked polypeptide sequences and a set of N ranked polypeptide sequences that best match features of the one or more mass spectra;
    subtracting synthetic spectra corresponding to each of the M ranked polypeptide sequences and to each of the N ranked polypeptide sequences from the one or more mass spectra so as to provide a first set and a second set of modified mass spectra, respectively;
    searching the database of polypeptide fragments of the second fragment pair type and the database of polypeptide fragments of the first fragment pair type so as to provide a third set and a fourth set of polypeptide sequences, respectively, wherein the third set and the fourth set of polypeptide sequences respectively provide best matches to features of the first and second sets of modified mass spectra; and
    creating a cumulative ranking of the polypeptide sequences of the third and fourth sets of polypeptide sequences.

2. The method of claim 1, further comprising the steps of:
    identifying best candidate polypeptide matches to the one or more mass spectra according to the cumulative ranking; and
    outputting the best candidate polypeptide matches to a user.

3. The method of claim 1, further comprising the steps of:
    identifying best candidate polypeptide matches to the one or more mass spectra according to the cumulative ranking; and
    outputting the best candidate polypeptide matches to an output database of a tangibly-embodied computer writeable medium.

4. The method of claim 1, wherein the first fragmentation technique and the second fragmentation technique are performed in a same ion reaction cell.

5. The method of claim 1, wherein the first fragmentation technique is electron transfer dissociation and the second fragmentation technique is collision induced dissociation.

6. The method of claim 5, wherein the electron transfer dissociation and the collision induced dissociation are performed in a same ion reaction cell.

7. The method of claim 1, wherein the first fragment pair type comprises b-type fragments and y-type fragments and wherein the second fragment pair type comprises c-type fragments and z-type fragments.

8. The method of claim 1 wherein the mass analyzer comprises a multipole ion trap.

9. The method of claim 1 wherein the mass analyzer comprises an electrostatic ion trap.

10. The method of claim 1, wherein the mass analyzer comprises a time-of-flight mass analyzer.

11. A system comprising:
 a source of sample ions;
 one or more ion traps or ion reaction cells fluidically coupled to the source of sample ions;
 a mass analyzer fluidically coupled to the one or more ion traps;
 a computer processor electronically coupled to the mass analyzer; and
 a tangibly-embodied computer-readable medium having computer-executable instructions encoded therein, said instructions operable to cause the computer processor to:
  cause the source of sample ions to provide a set of sample ions;
  cause the set of sample ions to be transferred to the one or more ion traps;
  cause the one or more ion traps to fragment selected ions of the set of sample ions using a first fragmentation technique and using a second fragmentation technique so as to create a first set and a second set of fragmented ions, respectively;
  cause the mass analyzer to receive a mixture of the first and second sets of fragmented ions;
  cause the mass analyzer to provide one or more mass spectra of the mixture of the first and second sets of fragmented ions to the computer processor;
  search a database of polypeptide fragments of a first fragment pair type and a database of polypeptide fragments of a second fragment pair type so as to respectively provide a set of M ranked polypeptide sequences and a set of N ranked polypeptide sequences that best match features of the one or more mass spectra;
  subtract synthetic spectra corresponding to each of the M ranked polypeptide sequences and to each of the N ranked polypeptide sequences from the one or more mass spectra so as to provide a first set and a second set of modified mass spectra, respectively;
  search the database of polypeptide fragments of the second fragment pair type and the database of polypeptide fragments of the first fragment pair type so as to provide a third set and a fourth set of polypeptide sequences, respectively, wherein the third and the fourth set of polypeptide sequences respectively provide best matches to features of the first and second sets of modified mass spectra; and
  create a cumulative ranking of the polypeptide sequences of the third and fourth sets of polypeptide sequences.

12. The system of claim 11, wherein said instructions are further operable to cause the computer processor to:
 identify best candidate polypeptide matches to the one or more mass spectra according to the cumulative ranking; and
 output the best candidate polypeptide matches to a user.

13. The system of claim 11, wherein said instructions are further operable to cause the computer processor to:
 identify best candidate polypeptide matches to the one or more mass spectra according to the cumulative ranking; and
 output the best candidate polypeptide matches to an output database of a tangibly-embodied computer writeable medium.

14. The system of claim 11, wherein the first fragment pair type comprises b-type fragments and y-type fragments and wherein the second fragment pair type comprises c-type fragments and z-type fragments.

15. The system of claim 11 wherein the mass analyzer comprises a multipole ion trap.

16. The system of claim 11 wherein the mass analyzer comprises an electrostatic ion trap.

17. The system of claim 11, wherein the mass analyzer comprises a time-of-flight mass analyzer.

* * * * *